United States Patent [19]

Sturman et al.

[11] Patent Number: 4,863,435
[45] Date of Patent: Sep. 5, 1989

[54] SAFETY HYPODERMIC SYRINGE

[76] Inventors: Martin F. Sturman, 7315 Granite Rd., Melrose Park, Pa. 19126; I. Martin Spier, 50 Park Ave., New York, N.Y. 10016

[21] Appl. No.: 235,466

[22] Filed: Aug. 24, 1988

[51] Int. Cl.$^4$ ............................................. A61M 5/32
[52] U.S. Cl. .................................. 604/198; 604/263; 604/192
[58] Field of Search ................. 604/198, 263, 187, 110

[56] References Cited

U.S. PATENT DOCUMENTS 4,664,654 5/1987 Strauss ................................ 604/198
4,795,432 1/1989 Karczmer .......................... 604/110

Primary Examiner—John D. Yasko
Attorney, Agent, or Firm—Michael Ebert

[57] ABSTRACT

A hypodermic syringe provided with a safety hypodermic needle and shield assembly to obviate the danger of a handler thereof being accidentally pricked by the point of the needle after it has been injected in a patient and then withdrawn, the withdrawn needle possibly being contaminated with infectious microorganisms. The assembly includes a needle-supporting hub receivable in a socket formed at the front end of a fluid chamber having a projecting nozzle which is inserted in the hub to communicate with the needle. Integral with the hub is a cup-like pedestal on which is anchored a compressible helical spring that surrounds the needle and terminates in a shield having a bore therein to permit the needle to pass therethrough, the normal length of the spring being such as to place the shield just above the point of the needle. In the retracted mode of the assembly, the spring is compressed to retract the shield which is then held by a releasable latching mechanism supported on the pedestal, thereby exposing the needle to permit its use. After the needle is injected in a patient and withdrawn, the shield is unlatched to cause the assembly to assume its extended mode in which the shield covers the point of the needle to prevent human contact therewith.

10 Claims, 3 Drawing Sheets

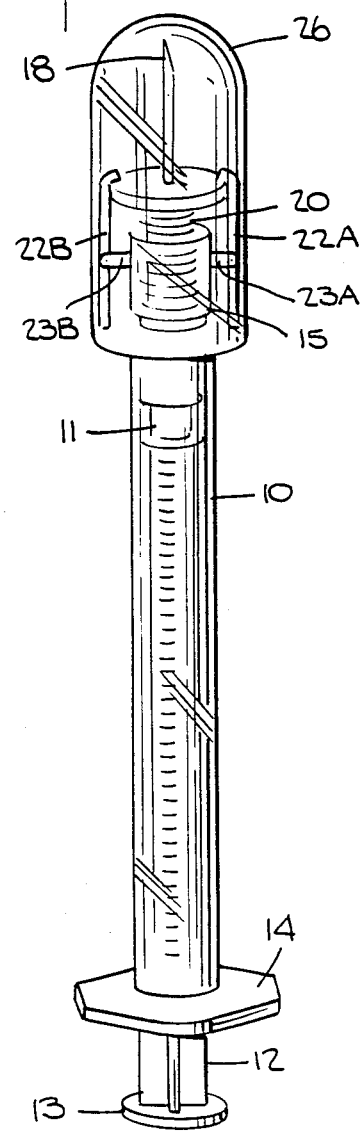
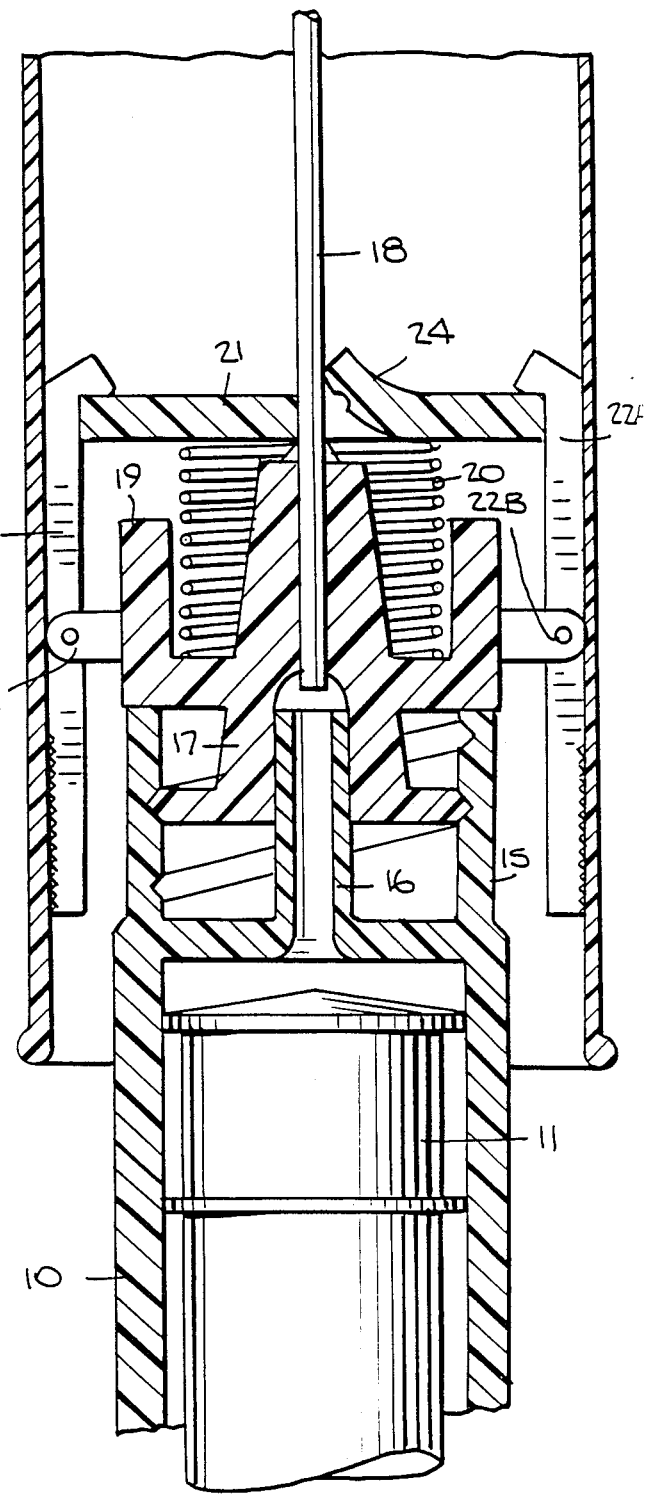
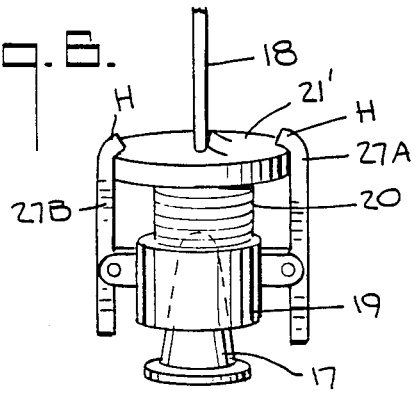

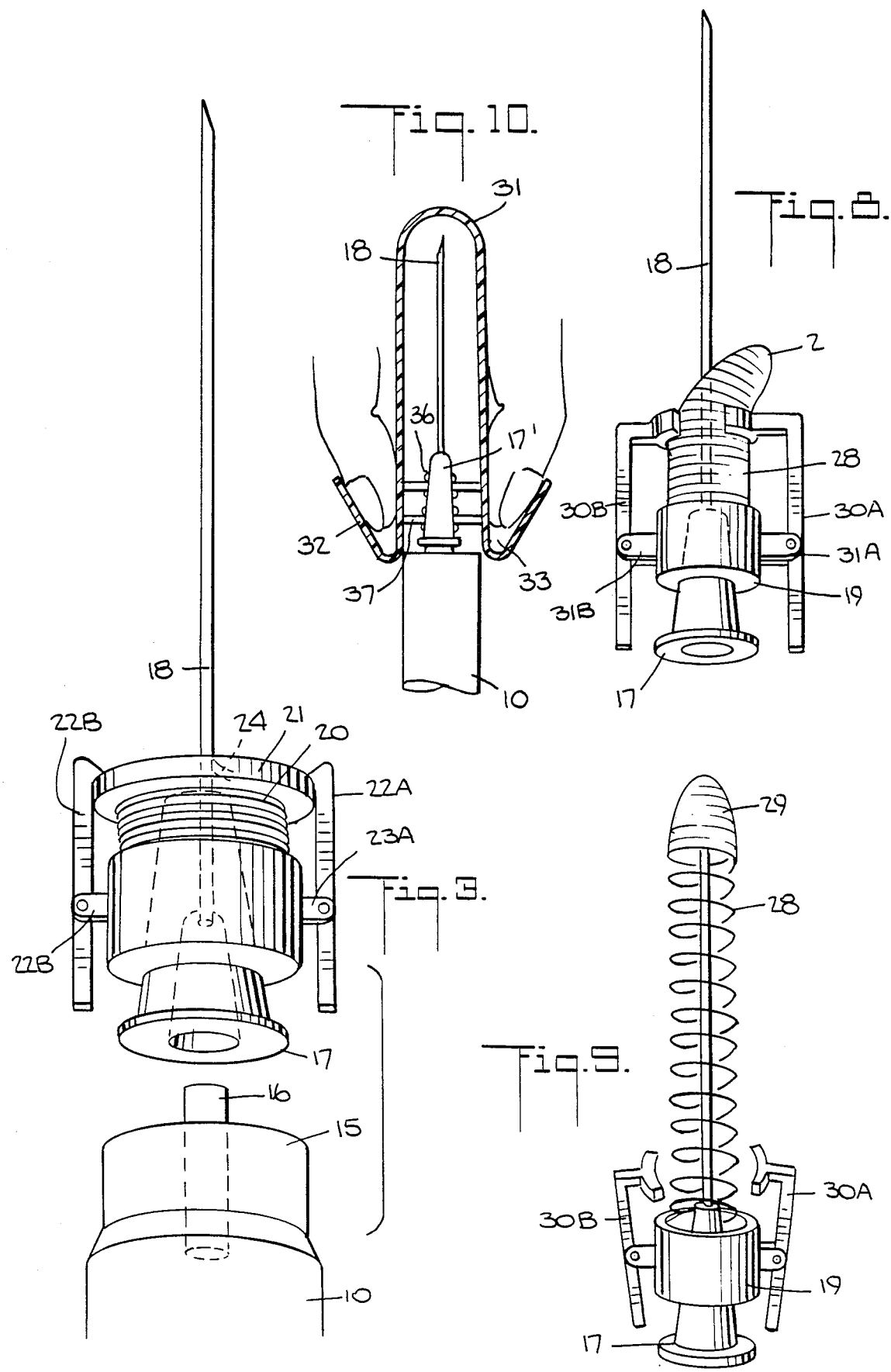

SAFETY HYPODERMIC SYRINGE

BACKGROUND OF INVENTION

1. Field of Invention

This invention relates generally to hypodermic syringes, and in particular to a safety hypodermic needle and shield assembly for a hypodermic needle to permit its use, the assembly when unlatched assuming an extended mode in which the shield protectively covers the point of the needle to prevent accidental sticks thereby.

2. Status of Prior Art

A hypodermic needle is usable for intravenous, subcutaneous and intramuscular injection of fluids, or the removal of blood (venipuncture), body fluids or abnormal collections thereof, the needle being of hollow construction and having a slanted open point. When the needle is mounted on a syringe, it is adapted to aspirate or inject fluids for diagnostic or therapeutic purposes.

Disposable hypodermic needles are now mass produced at low cost, many billions of such syringes being used every year in the health care field. While the modern hypodermic syringe now includes a fluid chamber molded of synthetic plastic material rather than glass, the basic design of this widely used medical appliance remains much as it was in 1853 when it was invented by Charles Pravaz, a French physician.

In a hypodermic syringe of standard design, a piston is slidable within a cylindrical fluid chamber, the shank of the piston extending beyond the open rear end of the cylinder and terminating in a handle. The front end of the chamber is provided with a projecting nozzle that is coaxial with an internally-threaded socket adapted to receive a needle-supporting hub. When the hub is screwed into the socket, the nozzle is then received therein to communicate with the needle.

A hypodermic needle and a syringe attached thereto are distributed in sterile condition within a plastic bubble package and to protect them against contamination in storage and shipment. In addition, the needle is enclosed in a removable overcap whose inlet end snaps onto the needle hub. Thus, after the hypodermic needle and syringe are removed from its package, in order to put it to use one must first remove the overcap to expose the needle. After the hypodermic syringe has been injected into a patient and then withdrawn, it is the usual practice before discarding the syringe to place the overcap back on the needle hub so that those thereafter handling discarded syringes for purposes of disposal will not be pricked thereby.

When a sterile hypodermic needle is injected into a patient suffering from hepatitis or other infectious disease, when the needle is then withdrawn from the patient, it may be contaminated with infectious agents. Hence, should the handler inadvertently prick himself with this contaminated needle, the consequences may be serious.

The possibility of accidental contamination by needle puncture of the skin of those individuals in the health care field who employ hypodermic syringes for venipuncture, the withdrawal of body fluids or for any other medical purpose is fairly high and represents a significant risk. Thus, physicians, nurses, laboratory personnel, paramedics and other involved in the care and treatment of patients are in danger of being accidentally inoculated with infectious microorganisms by contaminated needles.

Most accidental needle sticks occur when the needles are being recapped; for to do so properly, one must first align the needle with the relatively small diameter inlet of the overcap. Should the needle be misaligned, as may well happen should the handler be careless, distracted or fatigued, the point of the needle will not enter the overcap but may instead puncture the finger of the handler.

It is well established that in the last 25 years the risks involved in handling hypodermic syringes has markedly increased. Statistics indicate very high rates of hepatitis B infection among medical and laboratory personnel by reason of this accidental mode of disease transmission. The results of positive hepatitis surface antigen testing reveals a five-to-fifteen fold increase in the risk of developing the antigen and antibody (as well as chronic hepatitis) among surgeons and other health care personnel dealing with patients belonging to high risk groups, such as patients undergoing renal dialysis, drugicts, and the like. In a recent issue of the newsletter, Biomedical Business International, it is reported that there are between 800,000 and one million accidental needle sticks each year.

Medical personnel who care for patients suffering from AIDS run a still higher risk; for a needle contaminated with HIV (Human immunodeficiency virus) is a source of great danger. Should the handler of this needle be accidentally punctured, he faces the prospect of contracting a disease currently having a 100% mortality rate as compared, say, to the 5 to 10% mortality rate for hepatitis B.

Yet, in the prior art, it was only in recent years that patents have issued dealing with expedients to prevent accidental needle sticks. Thus, the expired patents Bauer, U.S. Pat. Nos. 2,674,246; White, 2,876,770; Saenz, 3,046,985; and Armao, 3,134,380, through dealing with hypodermic syringes are mainly concerned with the fact that most patients are frightened by the mere appearance of a hypodermic syringe. Patients object to being punctured by a sharp needle, even though it is a relatively painless experience. To overcome this fear, these patents provide a guard to conceal the needle so that it is never seen by the patient, even as he is being injected. Thus, the White patent provides a spring-biased guard which normally covers the needle. But when the needle is injected in a patient, the nose of the guard presses against the tissue and the spring is compressed to permit the needle to project out of the guard into the tissue.

The 1988 patent to Wanderer et al., U.S. Pat. No. 4,731,059, is concerned with preventing needle sticks, and for this purpose provides a shield which is slidable from a position covering the needle to a position overlying the fluid chamber so that the needle can be exposed when put to use and thereafter shielded. A somewhat similar arrangement is disclosed in the 1987 patent to Fox, U.S. Pat. No. 4,695,274, which shows a retractable safety jacket for a hypodermic needle.

One practical problem with the safety shields or needle guards of the type disclosed in the Wanderer et al. and Fox patents is that when the needle is exposed so that the syringe can be put to use, the retracted guard then covers and obscures the transparent chamber which is graduated so that one can determine the amount of fluid that is contained therein. Hence this guard interferes with the proper operation of the hypodermic syringe.

But the more serious drawbacks of prior art needle guard arrangements is that they require a modification of the basic configuration of the standard hypodermic syringe to accommodate the guard. Thus in one commercially-available form of safety hypodermic syringe, in order to accommodate a needle guard, the needle is mounted on an elongated extension rod projecting from the fluid chamber, so that when the guard is retracted, it overlies the extension rod, not the fluid chamber. Hence, fluid from the chamber must be conducted through the extension rod which by its very nature elongates the hypodermic syringe, making it more difficult to handle. Also, the extension tube will retain and waste an excessive amount of fluid.

SUMMARY OF INVENTION

In view of the foregoing, the main object of this invention is to provide a safety hypodermic needle and shield assembly for a syringe which obviates the danger of a handler thereof being accidentally pricked by the point of the needle after it has been injected in a patient and then withdrawn.

More particularly, an object of this invention is to provide a safety hypodermic needle and shield assembly of the above type which requires no basic modification of the design of a standard syringe and which can be manufactured inexpensively on a mass production basis.

Also an object of the invention is to provide an assembly of the above type which can readily be coupled to the fluid chamber of a standard hypodermic syringe.

Briefly stated, these objects are attained in a hypodermic syringe provided with a safety hypodermic needle and shield assembly to obviate the danger of a handler thereof being accidentally pricked by the point of the needle after it has been injected in a patient and then withdrawn, the withdrawn needle possibly being contaminated with infectious microorganisms. The assembly includes a needle-supporting hub receivable in a socket formed at the front end of a fluid chamber having a projecting nozzle which is inserted in the hub to communicate with the needle. Integral with the hub is a cup-like pedestal on which is anchored a compressible helical spring that surrounds the needle and terminates in a shield having a bore therein to permit the needle to pass therethrough, the normal length of the spring being such as to place the shield just above the point of the needle. In the retracted mode of the assembly, the spring is compressed to retract the shield which is then held by a releasable latching mechanism supported on the pedestal, thereby exposing the needle to permit its use. After the needle is injected in a patient and withdrawn, the shield is unlatched to cause the assembly to assume its extended mode in which the shield covers the point of the needle to prevent human contact therewith.

BRIEF DESCRIPTION OF DRAWINGS

For a better understanding of the invention as well as other objects and further features thereof, reference is made to the following detailed description to be read in conjunction with the accompanying drawing, wherein:

FIG. 1 illustrates, in perspective, a hypodermic syringe provided with one preferred embodiment of a safety hypodermic needle and shield assembly in accordance with the invention, the assembly being shown in its retracted mode;

FIG. 2 is an enlarged sectional view of the retracted assembly;

FIG. 3 is an enlarged perspective view of the assembly in its retracted mode and of the socket of the fluid chamber to which the assembly is coupled;

FIG. 6 illustrates a second preferred embodiment of an assembly which is shown in its retracted mode;

FIG. 8 illustrates a third preferred embodiment of an assembly which is shown in its retracted mode;

FIG. 9 shows this assembly in its extended mode; and

FIG. 10 illustrates an improved overcap in accordance with the invention.

DETAILED DESCRIPTION OF INVENTION

First Embodiment

Figure 4:
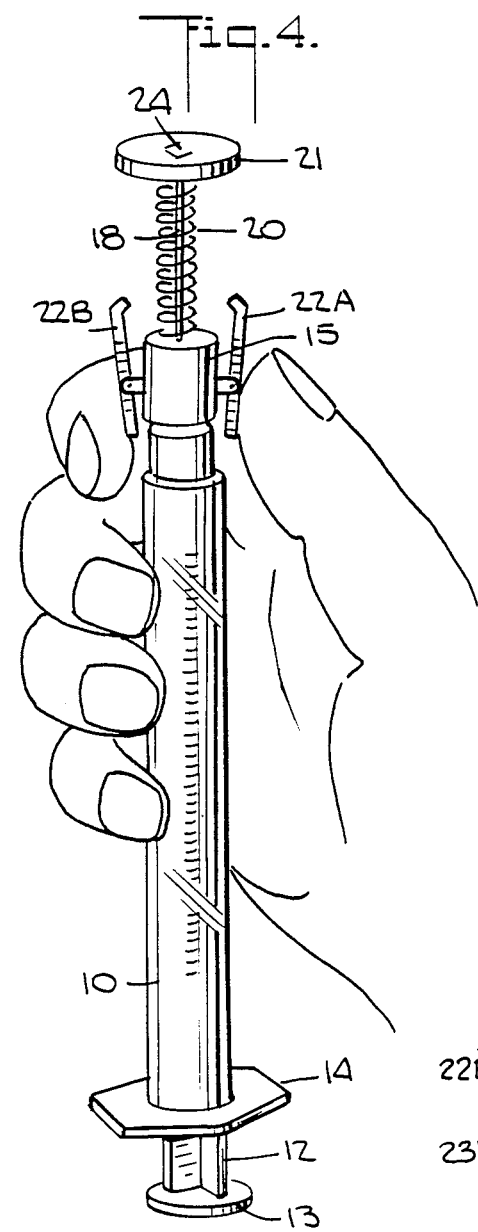
FIG. 4 shows the assembly in the hands of a user who has unlatched it to cause the assembly to assume its extended mode.

Referring now to FIGS. 1 to 3 of this drawing, shown therein is a hypodermic syringe provided with a safety hypodermic needle and shield assembly in accordance with the invention. The assembly in its retracted mode, which is the mode shown in FIGS. 1 to 3, exposes the hypodermic needle to permit its injection into a patient. In its extended mode, the assembly acts to shield the point of the needle to prevent an accidental stick.

Included in the syringe is a cylindrical fluid chamber 10 formed of transparent, synthetic plastic material such as polyethylene, polypropylene, polystyrene or PVC having indicia thereon to indicate the level of fluid in the chamber. Slidable within the chamber is a piston 11 for ejecting fluid from the chamber or drawing fluid therein, the piston having a shank 12 which extends beyond the open end of the chamber and terminates in a handle 13.

As is conventional, the rear end of chamber 10 is provided with a flange 14 so that to manipulate the piston to draw fluid from a patient or to inject fluid into the patient, the user holds the flange with the fingers of one hand while grasping handle 13 with fingers of the other hand.

At the front end of chamber 10 is an internally-threaded cylindrical socket 15 and coaxially disposed therein is a nozzle 16 whose inlet communicates with the interior of the chamber. Threadably received in socket 15 is a tapered needle-supporting hub 17, nozzle 16 entering the hollow base section of the hub to communicate with a hypodermic needle 18 supported at the apex of the hub.

Integral with hub 17 is a cup-shaped pedestal 19 which when the base section of the hub is screwed into socket 15 is then seated on the rim thereof to provide a stable support for the needle and for a compressible helical spring 20 which surrounds needle 18. Spring 20, which is preferably formed of stainless steel, is anchored at its lower end on pedestal 19, the upper end of the spring supporting a disc-shaped shield 21 whose diameter is greater than that of the pedestal. Shield 21 is provided with a center bore to permit the needle to pass therethrough. In practice, the shield, the pedestal and the disc and all other elements of the assembly other than the spring and needle are molded of a suitable synthetic plastic such as polypropylene.

In the retracted mode of the assembly, spring 20 is compressed to expose needle 18, and shield 21 is latched at a retracted position adjacent the apex of hub 17 to maintain the spring in its compressed state. The latching mechanism for this purpose in the first embodiment is constituted by a pair of toggles 22A and 22B hingedly mounted at diametrically-opposed positions on brackets 23A and 23B integral with the cylindrical shell of the cup-shaped pedestal 19. The hinges for this purpose are preferably in the form of torsion bars integral with brackets 23A and 23B, although other forms of spring-biased hinges may be used for the toggles. The upper end of the toggles are hook-shaped to engage shield 21.

Shield 21 is provided with a trap door 24 to shut the bore therein in the extended mode of the assembly when the latching mechanism is released and the disc is then raised by spring 20 to a position just above the point of the needle. In the embodiment shown, trap door 24 is in the form of a flexible flap having a recess 25 at its underside to receive the point of the needle when the trap door is shut. In practice, instead of a deflectable flap, the trap door may be slidable and supported by crossed flexible bars to permit its retraction relative to the bore.

The assembly includes an overcap 26 of synthetic plastic material having a diameter which permits the overcap to frictionally engage toggles 22A and 22B in their vertical latching state, as shown in FIG. 1. Hence the overcap acts not only to enclose and protect the needle but also to ensure that the assembly is maintained in its retracted mode during shipment and storage. Because the overcap houses the entire assembly, it is a simple matter, by holding the overcap, to then screw the assembly onto the socket of the fluid chamber.

In practice, therefore, the capped assembly may be separately packaged, and used in conjunction with syringes of various sizes, as long as these syringes include a fluid chamber socket adapted to receive the hub of the safety needle and shield assembly. The assembly itself may be made with needles of different gauges and in different dimensions appropriate to the syringes to which the assemblies are to be coupled.

Figure 5:
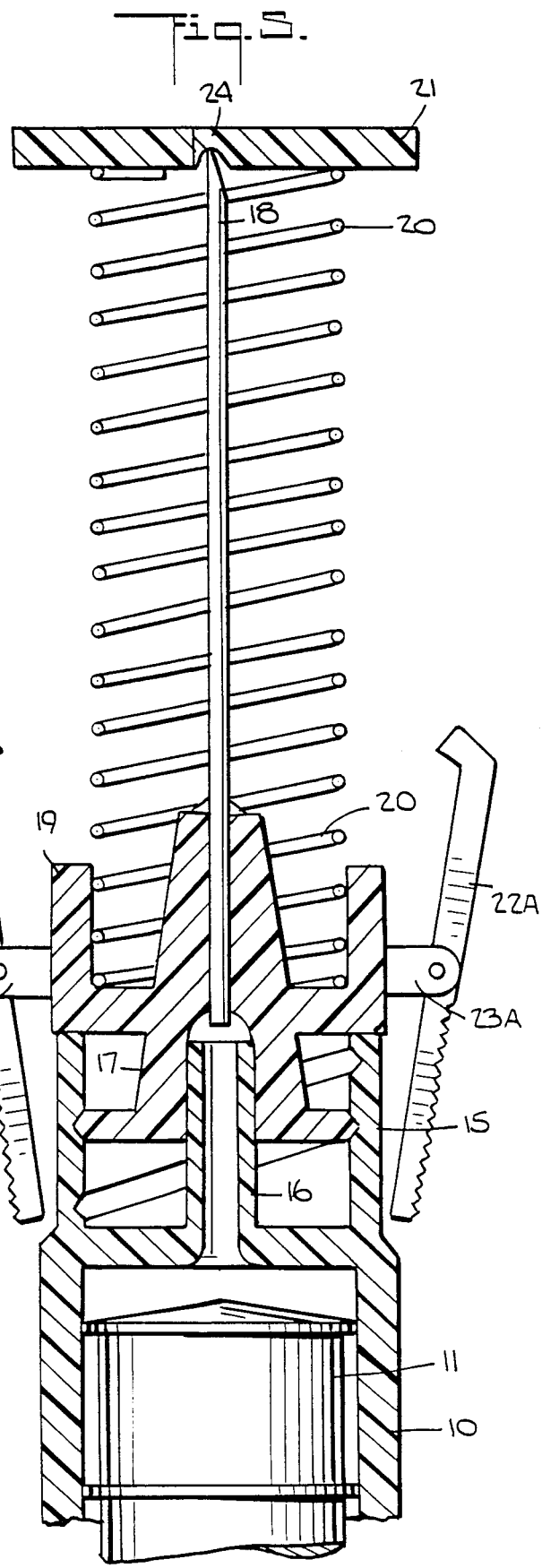
FIG. 5 is a section taken through the assembly in its extended mode.

When the hypodermic syringe in accordance with the invention is to be used, overcap 26 is removed to expose needle 18 of the retracted safety shield assembly, and the patient is then injected with the needle. After the needle is withdrawn from the patient, the individual who is holding the syringe in his hand then uses his fingers, as shown in FIGS. 4 and 5, to operate toggles 22A and 22B to release shield 21 which is then raised by spring 20 to a position just above the point of the needle, thereby protecting the individual from being pricked by the point of the needle. It is no longer necessary, as with conventional hypodermic syringes, to place the overcap back on the syringe, although one may do so.

Second Embodiment

Figure 7:
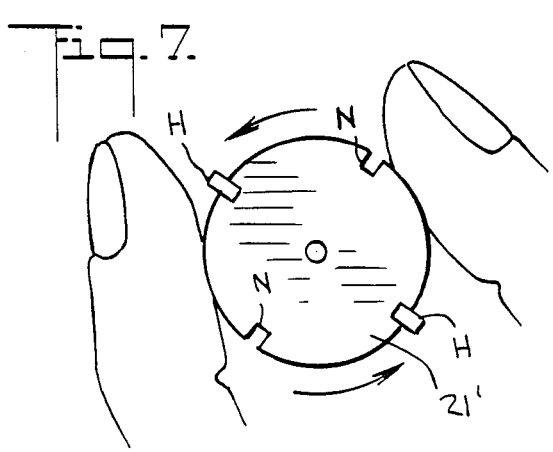
FIG. 7 is a top view of the shield included in the FIG. 6 assembly.

In the safety shield assembly shown in FIGS. 6 and 7, instead of spring-biased toggles as in the first embodiment, the shield 21' supported at the upper end of helical spring 20 is held in its retracted position by a pair of fixed latching arms 27A and 27B which are integral with cup-shaped pedestal 19, the arms having hooks H at their upper ends which engage the disc-shaped shield.

Shield 21' is provided with a pair of diametrically opposed notches N, so that by turning the shield to an angular position at which the notches register with hooks H, the hooks fall into these notches and the shield is then released from the latching arms to permit the assembly to assume its extended mode. In all other respects, the assembly functions in the same manner as in the first embodiment.

Third Embodiment

In the embodiment shown in FIGS. 8 and 9, spring 28 surrounding needle 18, instead of terminating in a separate shield, as in the prior embodiments, is so convoluted at its upper end as to create a coiled conical shield 29 in which the convolutions are of progressively smaller diameter.

In its retracted mode, as shown in FIG. 8, spring 28 is compressed, needle 18 going through the space between adjacent conical shield is now offset with respect to the needle. The spring is held in the retracted mode by a pair of spring-biased toggles 30A and 30B hingedly supported on brackets 31A and 31B secured at diametrically-opposed positions on pedestal 19. The upper ends of the toggles are provided with arcuate shoes S to engage the spring and maintain it in its compressed state. When these toggles are operated by the fingers of the handler as shown in FIG. 9, the spring is released to cause shield 29 to assume a protective position just above the point of the needle, this being the extended mode of the assembly.

While there have been shown and described preferred embodiments of a safety hypodermic syringe in accordance with the invention, it will be appreciated that many changes and modifications may be made therein without, however, departing from the essential spirit thereof.

Improved Overcap

As pointed out previously, most accidental needle sticks occur when a hypodermic needle, after being withdrawn from a patient is being recapped. Because the inlet of the conventional overcap is of relatively small diameter, the user may have difficulty in aligning the point of the needle with the inlet, and a misaligned needle instead of entering the inlet may puncture a finger of the handler.

Overcap 26 shown in FIG. 1 is of relatively enlarged diameter, and to this degree reduces the possibility of accidental sticks. It is also known to provide a safety needle sheath or overcap having a funnel-shaped receiving end (see Pedicano et al. U.S. Pat. No. 4,610,667). But an overcap of this design does not fully protect the fingers of the user.

In the overcap 31 shown in FIG. 10, the diameter of this sheath is about the same as the diameter of the cylindrical chamber 10 of the syringe, and is therefore much greater than the diameter of a conventional overcap. The inlet end 31A of overcap 31 is outwardly flared and curved to provide a radiused entry which is integral with a frusto-conical gauntlet 32. This gauntlet defines an annular pocket 33 for receiving fingers 34 of the user. Gauntlet 33 may be buttressed by internal ribs at diametrically opposed positions extending between the inner wall of the gauntlet and the outer wall of the overcap.

The hub 17' on which needle 18 is mounted is so molded as to form detents 36 on its exterior wall. These detents are engaged by flexible fingers 37 that are molded on the inner wall of the overcap. The relationship of the flexible fingers to the detents is such as to provide a frictional fit, the fingers flexing to permit the overcap to be fitted onto the hub or withdrawn therefrom. Or the detents may be angled relative to the flexible fingers to permit a screw-like action for fitting the overcap onto the hub or for withdrawing it from the hub.

Hence the gauntlet acts as a protective shield for the user's fingers, while the oversize receiving end of the overcap with its radiused inlet greatly reduces the possibility of the needle failing to enter the overcap, even when this operation is carried out carelessly. In practice, the portion of the overcap beyond the finger pressure point may be reduced in diameter to about the diameter of the existing overcap which is just sufficient to protect the needle, thereby effecting a substantial saving in material.

We claim:

1. In combination with a standard syringe whose fluid chamber has a piston slidable therein and is provided at its front end with a projecting nozzle and a cylindrical, internally-threaded socket concentric therewith; a safety hypodermic needle and shield assembly adapted to prevent accidental stick by the point of the needle after the needle has been injected into a patient and then withdrawn, said assembly comprising:

a hub provided with a hollow base and an apex thereabove to support the needle, said base being threadably receivable in the socket of the syringe whereby the nozzle is then received in the hollow base to communicate with the needle to conduct fluid from the chamber into the needle or to conduct fluid from the needle into the chamber;

B a pedestal integral with the hub to support a spring;

C a compressible helical spring surrounding the needle, the lower end of the spring being anchored on the pedestal;

D a shield supported at the upper end of the spring whose normal length is such as to place the shield just above the point of the needle, said shield having a center opening therein to permit the needle to pass therethrough;

E a releasable latching mechanism supported on the pedestal which in a retracted mode of the assembly when the spring is compressed to retract the shield is adapted to hold the shield at its retracted position at which the needle is exposed for use, and in an extended mode of the assembly when the mechanism is released causes the shield to assume its place above the point to prevent accidental stick; and F a removable overcap which in the retracted mode of the assembly protectively covers the needle and surrounds the releasable latching mechanism to prevent accidental release thereof, thereby ensuring that the assembly is maintained in its retracted mode during shipment and storage.

2. An assembly as set forth in claim 1, wherein said shield is provided with a trap door which when the shield is in place above the point of the needle is automatically shut to block the opening in the shield.

3. An assembly as set forth in claim 2, wherein said door has a recess on its underside to receive the point of the needle.

4. An assembly as set forth in claim 1, wherein said spring is made of stainless steel.

5. An assembly as set forth in claim 1, wherein said latching mechanism is constituted by a pair of spring-biased toggles pivotally supported at opposed positions on said pedestal and having hooks at their upper ends to engage the shield.

6. An assembly as set forth in claim 5, wherein said toggles are mounted on torsion bars.

7. An assembly as set forth in claim 5, wherein said removable overcap frictionally engages the toggles.

8. An assembly as set forth in claim 1, wherein said latching mechanism is constituted by a pair of upright arms supported on tee pedestal and having hooks at their upper ends to engage the shield, said shield being rotatably supported on the spring and having notches therein which when in registration with the hooks, releases the shield.

9. An assembly as set forth in claim 1 wherein said shield is constituted by the upper section of the spring which is so convoluted as to create a coiled conical shield.

10. An assembly as set forth in claim 1, wherein said removable overcap is configured to house said assembly and to frictionally engage said latching mechanism so that the assembly may be handled as a unit and screwed onto the socket of the syringe.

* * * * *

UNITED STATES PATENT AND TRADEMARK OFFICE
CERTIFICATE OF CORRECTION

PATENT NO. : 4,863,435
DATED : September 5, 1989
INVENTOR(S) : Martin F. Sturman and I. Martin Spier It is certified that error appears in the above-identified patent and that said Letters Patent is hereby corrected as shown below:

Column 8, line 29, "tee" should read --the--

Signed and Sealed this

Eighth Day of January, 1991

Attest:

HARRY F. MANBECK, JR.

*Attesting Officer*     *Commissioner of Patents and Trademarks*